(12) United States Patent
Billeres et al.

(10) Patent No.: US 8,994,376 B2
(45) Date of Patent: Mar. 31, 2015

(54) DETECTION METHOD AND DETECTOR OF A DISRUPTION, POSITIONING METHOD AND SYSTEM USING SAID METHOD

(75) Inventors: Malvina Billeres, Grenoble (FR); Viviane Cattin, Saint Egreve (FR)

(73) Assignee: Commissariat a l'Energie Atomique et aux energies alternatives, Paris (FR)

( * ) Notice: Subject to any disclaimer, the term of this patent is extended or adjusted under 35 U.S.C. 154(b) by 530 days.

(21) Appl. No.: 13/322,290

(22) PCT Filed: May 6, 2010

(86) PCT No.: PCT/EP2010/056211
§ 371 (c)(1),
(2), (4) Date: Dec. 27, 2011

(87) PCT Pub. No.: WO2010/136316
PCT Pub. Date: Dec. 2, 2010

(65) Prior Publication Data
US 2012/0092004 A1    Apr. 19, 2012

(30) Foreign Application Priority Data
May 26, 2009 (FR) ...................................... 09 53462

(51) Int. Cl.
*G01V 3/00* (2006.01)
*G01R 33/00* (2006.01)
*A61B 5/06* (2006.01)

(52) U.S. Cl.
CPC ........................................ *A61B 5/062* (2013.01)
USPC .............................. 324/329; 324/260; 324/335

(58) Field of Classification Search
USPC ................................................. 324/326, 329
See application file for complete search history.

(56) References Cited

U.S. PATENT DOCUMENTS

| | | | |
|---|---|---|---|
| 6,172,499 | B1 | 1/2001 | Ashe |
| 6,528,989 | B1 | 3/2003 | Hansen |
| 2002/0093338 | A1 | 7/2002 | Rowan |
| 2003/0187337 | A1 | 10/2003 | Tarassenko et al. |
| 2008/0033282 | A1 | 2/2008 | Bar-Tal et al. |
| 2008/0125646 | A1 | 5/2008 | Govari et al. |

FOREIGN PATENT DOCUMENTS

| | | |
|---|---|---|
| EP | 0993804 | 4/2000 |
| EP | 1502544 | 2/2002 |
| JP | H05128342 | 5/1993 |
| JP | 2004251712 | 9/2004 |
| JP | 2008002202 | 1/2008 |
| WO | WO 2004/091391 | 10/2004 |

*Primary Examiner* — Bot Ledynh
(74) *Attorney, Agent, or Firm* — Occhiuti & Rohlicek LLP

(57) ABSTRACT

This method for detecting a disturber of magnetic field amplitude comprises:

the emitting (62) of several magnetic fields of different frequencies from a same uniaxial magnetic field source, the amplitudes of the magnetic field emitted at two different unspecified frequencies being related to each other by a predetermined ratio, the measurement (64) of the amplitude of these magnetic fields at different frequencies by means of a same sensor, and the reporting (70) of an amplitude disturber if a ratio between two of said measured amplitudes diverges from a predetermined threshold of the predetermined ratio which relates the amplitudes of the magnetic fields emitted at the same frequencies and, if not, the absence of any reporting.

10 Claims, 2 Drawing Sheets

DETECTION METHOD AND DETECTOR OF A DISRUPTION, POSITIONING METHOD AND SYSTEM USING SAID METHOD

CROSS REFERENCE TO RELATED APPLICATIONS

This application is the national stage entry under 35 USC 371 for PCT/EP2010/056211, filed May 6, 2010, which claims the benefit of the May 26, 2009 priority date of French Application No. 953462. The contents of both the foregoing applications are incorporated herein by reference.

The invention relates to a method of detection and to a detector of a disturber of the amplitude of a magnetic field in proximity to a source of this magnetic field. The invention also relates to a method and a system for localizing an object in a referential system using this detection method.

A magnetic field amplitude disturber is defined herein as being any object that degrades or deforms the field lines of a magnetic field emitted in proximity. For example, the disturber may be a conductive part. In this case, the degradation of the magnetic field lines is caused by the appearance of eddy currents in the conductive part. The conductive part may be for example a metal part. The disturber may also be a magnetic part such as a paramagnetic or ferromagnetic part. In the case of ferromagnetic parts, the deterioration of the amplitude of the magnetic field is due to the fact that this element deforms the lines of the magnetic field.

For example, known methods for detecting disturbers are used as part of methods for localizing an object in a referential system by means of at least one measurement pair. Each measurement pair comprises:
  a uniaxial source capable of emitting magnetic fields at several frequencies, and
  a sensor capable of measuring the amplitude of the magnetic fields emitted by this uniaxial source,
  one among the uniaxial source and the sensor being linked to the referential system while the other among the uniaxial source and the sensor being linked to the object.

A uniaxial magnetic field source is a source that emits the magnetic field essentially along only one axis. For example, a coil whose turns are wound about a same axis is a uniaxial magnetic field source and the preferred emission axis coincides with the winding axis of the turns.

Here below in this description the term "amplitude" of the magnetic field refers to the amplitude A of the field in phase or the amplitude Ch of the modulus of the field which is a function both of the field in phase and of the field in quadrature-phase. These amplitudes A and Ch are proportional.

The amplitude A is given by the following relationship:

$$A = \sqrt{Ix^2 + Iy^2 + Iz^2} \quad (1)$$

where:
Ix, Iy and Iz are the in-phase components of the field, measured in three mutually orthogonal directions X, Y and Z.

The amplitude Ch is given by the following relationships:

$$Ch = \sqrt{Ch_x^2 + Ch_y^2 + Ch_z^2} \quad (2)$$

$$Ch_x = 2\sqrt{(Ix^2 + Qx^2)} \quad (3)$$

$$Ch_y = 2\sqrt{(Iy^2 + Qy^2)} \quad (4)$$

$$Ch_z = 2\sqrt{(Iz^2 + Qz^2)} \quad (5)$$

where:
Qx, Qy, Qz are the components in quadrature-phase of the magnetic field measured along three orthogonal directions X, Y and Z.

Typically, the sensor capable of measuring the amplitude of the magnetic field as defined here above is a triaxial sensor capable of measuring the components in phase and/or in quadrature-phase along the axes X, Y and Z. To localize the object, these methods comprise:
  the emission of a magnetic field at a given frequency by the uniaxial source and the measuring of this magnetic field by the sensor of the same pair,
  the localizing of the object in the referential system through measurements made by the measurement pair or pairs.

Such localizing methods are often used in medicine to localize a probe or a catheter within the human body. For such applications, the reliability of the localizing of the probe is very important. In the medical field, there are many magnetic disturbers capable of falsifying the localization. For example, the disturber may be an operation table, a surgeon's scalpel, the metal armature of another apparatus placed in proximity to the patient, etc.

Several methods have been proposed for detecting such disturbers (see for example EP 1 502 544 or EP 0 993 804). These methods use complex computations. Furthermore, in the method described in EP 0 993 804, a calibration, preliminary to any detection of a disturber, must be made.

The invention seeks to overcome this problem by simply detecting the presence of a disturber of the amplitude of the magnetic field emitted.

An object of the invention therefore is a method for detecting a disturber of magnetic field amplitude, comprising:
  the emitting of several magnetic fields of different frequencies from a same uniaxial magnetic field source, the amplitudes of the magnetic field emitted at two different unspecified frequencies being related to each other by a predetermined ratio,
  the measurement of the amplitude of these magnetic fields at different frequencies by means of a same sensor, and
  the reporting of an amplitude disturber if a ratio between the measured amplitudes diverges from a predetermined threshold of the predetermined ratio which relates the amplitudes of the magnetic fields emitted at the same frequencies and, if not, the absence of any reporting.

The above method uses the fact that a disturber does not disturb the amplitude of the magnetic field at all the frequencies in the same way. Typically, a disturber disturbs the amplitude of a magnetic field to a greater or to a lesser extent depending on the frequency considered.

The above method also uses the property of the magnetic fields according to which, in the absence of a disturber, the amplitude of the magnetic field measured by the sensor varies according to the distance R between itself and the uniaxial source of this magnetic field. This property is independent of the frequency of the magnetic field emitted. More specifically, the amplitude of the magnetic field measured decreases proportionally to $1/R^3$.

In the explanations here below, $A_i$ and $A_j$ denote the amplitudes of two magnetic fields emitted by a same uniaxial source, respectively at the frequencies $f_i$ and $f_j$. Also $Am_i$ and $Am_j$ denote the amplitudes measured by the sensor at the frequencies $f_i$ and $f_j$. The sensor is at a distance R from the uniaxial source.

When there is no disturber, the ratio $Am_i/Am_j$ must be substantially equal to the predetermined ratio $A_i/A_j$. Thus, a difference between these ratios that is above the predetermined threshold indicates the presence of a disturber of amplitude of the magnetic field. Furthermore, this remains true whatever is the distance R. It is therefore not necessary to know this distance R to detect a disturber.

Such a method does not require any complex computations since it is enough to simply compare measured amplitude ratios with a predetermined threshold.

This method also enables the detection of a disturber without making use of preliminary calibration, unlike in the case of prior art methods.

Finally, the use of a same uniaxial source to emit the magnetic fields at different frequencies augments the precision of the method because it is not necessary to correct differences due to the use of several uniaxial sources spaced out from one another so that each emits magnetic fields at different frequencies.

The embodiments of this detection method may comprise one or more of the following characteristics:

The ratios between the amplitudes of the magnetic fields emitted at the different frequencies are all equal;
the method comprises:
the synchronizing of the emission and the measurements of the magnetic fields of different frequencies to measure only the amplitude of the magnetic field in phase with the emitted magnetic field of the same frequency, and
the reporting or not reporting of a disturber of amplitude solely as a function of the measured amplitudes of the magnetic fields in phase;
the magnetic fields of different frequencies are emitted simultaneously.

These embodiments of the detection method furthermore have the following advantages:

emitting magnetic fields whose amplitude ratios are equal enables the detection of a disturber in comparing simply the ratios of amplitudes measured between each other without being necessary to have other information on the predetermined ratio;
measuring and using only the amplitude in phase of the magnetic fields simplifies the implementation of the method because it is then not necessary to measure the amplitude of these same magnetic fields in quadrature-phase;
simultaneously emitting the magnetic fields of different frequencies accelerates the detection of a disturber.

An object of the invention is also a method for localizing an object in a referential system by means of at least one measurement pair, this method comprising:

the detection of a disturber of amplitude of the magnetic field in using the uniaxial source and the sensor of a measurement pair to implement the above detection method, and
when the object is localized, the weighting of the measurement of the magnetic field obtained by this measurement pair as a function of the reporting or non-reporting of a disturber so as to limit the impact of a disturbed measurement made by this measurement pair on the localizing of the object.

The above method of localizing shows improved precision since the measurements made by the pairs of disturbed measurements are weighted to limit their impact on the localizing of the object. Furthermore, it is the same uniaxial source and the same sensor that are used both to detect a disturber and to localize the object.

The embodiments of the method of localizing may comprise the following characteristic:

the method comprises:
the emitting of magnetic fields and the measurement of these magnetic fields by means of more than nine measurement pairs, each measurement pair being distinguished from the others by the uniaxial source or the sensor used or by the frequency of the magnetic field measured and,
when the object is localized, the measurement by a measurement pair reported as being disturbed by a disturber is weighted so as to limit the impact of this disturbed measurement on the localizing of the object relatively to the non-disturbed measurements of the measurement pair.

This embodiment also has the advantage of enabling the determining of the position and the orientation of the object in a three-dimensional orthogonal referential system.

An object of the invention is also an information-recording medium comprising instructions to implement the above methods when these instructions are executed by an electronic computer.

An object of the invention is also a detector of a disturber of amplitude of a magnetic field, this detector comprising:

a uniaxial source of several magnetic fields of different frequencies in which the amplitudes of the magnetic fields emitted at two different unspecified frequencies are related to one another in a predetermined ratio,
a sensor to measure the amplitudes of these magnetic fields at different frequencies, and
an indicator capable of reporting the presence of a disturber of amplitude of the magnetic field only if a ratio between the measured amplitudes diverges from a predetermined threshold of the predetermined ratio which relates the amplitudes of the magnetic fields emitted at the same frequencies.

The embodiments of this detector may comprise the following characteristic:

the uniaxial source is constituted by a single coil whose turns are wound about a single winding axis.

Finally, an object of the invention is also a system for localizing an object in a referential system, this system comprising:

at least one measurement pair, each measurement pair comprising:
a uniaxial source capable of emitting magnetic fields at several frequencies, and
a sensor capable of measuring the amplitude of the magnetic fields emitted by this uniaxial source,
one among the uniaxial source and the sensor being linked to the referential system and the other among the uniaxial source and the sensor being linked to the object,
a localization module capable of localizing the object in the referential system from the measurements made by the measurement pair or pairs,
the above detector of a disturber of magnetic field amplitude disturbing this measurement pair, the uniaxial source and the sensor of this detector being common with those of the measurement pair, and
the localizing module is capable of weighting the measurement of the magnetic field made by this measurement pair as a function of the reporting or non-reporting of this disturber so as to limit the impact of a disturbed measurement made by this measurement pair on the localizing of the object.

The invention will be understood more clearly from the following description given purely by way of a non-restrictive example and made with reference to the appended drawings, of which:

In these figures, the same references are used to designate the same elements.

Here below in this description, the characteristics and functions well known to those skilled in the art are not described in detail.

Figure 1:
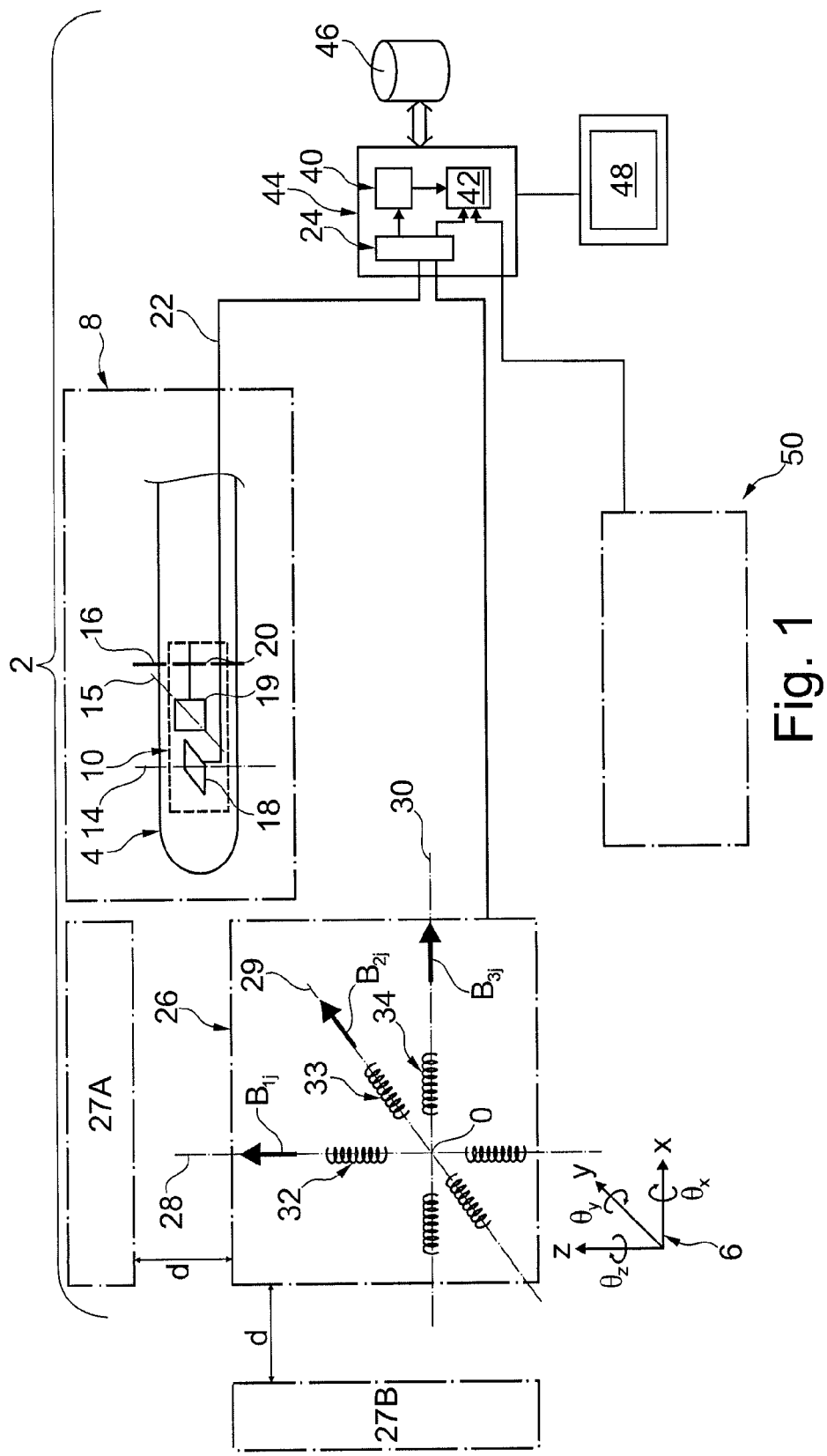
FIG. 1 is a schematic illustration of a system for localizing an object in a referential system comprising a detector of disturbers.

FIG. 1 represents a system 2 for localizing an object 4 in a referential system 6. The object 4 is for example a probe or a catheter introduced into a human body 8. The object 4 is mobile in the referential system 6.

The referential system 6 is a fixed referential system having three orthogonal axes X, Y and Z.

The localizing of the object 4 in the referential system 6 consists in finding its x, y, z position and its $\theta_x$, $\theta_y$ and $\theta_z$ orientation. The angles $\theta_x$, $\theta_y$ and $\theta_z$ represent the orientation of the object 4 respectively relatively to the axes X, Y and Z.

To enable the localizing of the object 4 in the referential system 6, this object is for example equipped with a sensor 10 of magnetic fields.

The sensor 10 is a triaxial sensor, i.e. a sensor capable of measuring the magnetic field received along three non-collinear axes 14 to 16. Here, these axes of measurement 14 to 16 are mutually orthogonal. These axes are linked to the object 4. To this end, the sensor 10 incorporates three uniaxial transducers 18 to 20. Each of these transducers has a direction of measurement along which its sensitivity to the magnetic field is the maximum. Here, the directions of measurement of the transducers 18, 19 and 20 coincide respectively with the axes 14, 15 and 16.

For example, the transducers 18, 19 and 20 are coils wound respectively about the axes 14, 15 and 16.

Each of these transducers is connected by means of a flexible wire link 22 to a processing unit 24.

The unit 24 is also connected to three triaxial sources 26, 27A and 27B of magnetic fields so as to have geometrical redundancy. These sources 26, 27A and 27B are spaced out from one another by a distance d. By way of an example, the sources 26, 27A and 27B are identical and only the source 26 is described in greater detail.

The source 26 is fixed in the referential system 6. This source 26 is capable of emitting magnetic fields along three orthogonal axes 28 to 30. Here, the axes 28 to 30 are respectively parallel to the axes Z, Y and X of the referential system 6.

To this end, the source 26 is herein formed by three uniaxial sources 32 to 34. The uniaxial sources 32 to 34 respectively emit fields $B_{1j}$, $B_{2j}$ and $B_{3j}$ along the directions 28, 29 and 30. The index i is an identifier of the uniaxial source and the index j is an identifier of the frequency $f_j$ of the magnetic field emitted by this uniaxial source.

Each of these uniaxial sources 32 to 34 can be modeled by a point source of magnetic fields. Preferably, the uniaxial sources 32 to 34 are laid out so that their point sources respectively occupy the same position in the referential system 6. Here, this position is identified by a point O. The point O is at the intersection of the axes 28 to 30.

For example each uniaxial source 32 to 34 consists of a single coil wound respectively about the axes 28 to 30. Here, each of these coils is divided into two identical groups of turns distributed symmetrically on either side of the point O along the winding axis. Each group of turns is coiled in the same sense along the winding axis.

The shortest distance between the triaxial source 26 and the triaxial sources 27A and 27B is at least twice and preferably three times greater than the greatest dimension of the source 26. The greatest dimension of the source 26 is for example herein the greatest length of one of the uniaxial sources 32 to 34.

The association of a single uniaxial source and a single triaxial sensor working at the same working frequency forms a measurement pair. For example, the uniaxial source 32 and the sensor 10 form a first measurement pair when they work at the frequency $f_{1f}$ and a second measurement pair when they work at the frequency $f_{2f}$. The same sensor 10 associated with the uniaxial source 33 forms a third and fourth measurement pair when they work respectively at the frequencies $f_{1f}$ and $f_{2f}$. In the embodiment described here, each uniaxial source works at two frequencies $f_{1f}$ and $f_{2f}$. There are therefore 18 measurement pairs.

The processing unit 24 supplies the source 26 with alternating current to generate the magnetic fields $B_{1j}$ and acquires the magnetic fields measured by the transducers 18 to 20. Here below in this description, it is assumed that the disturber is a non-conductive magnetic part. Typically, for each measurement pair, the unit 24 establishes the amplitude $Am_{1j}$ of the component I of the magnetic field in phase with the magnetic field emitted.

To this end, the unit 24 is a synchronous detector. An example of such a synchronous detector is described with reference to FIG. 16 of the U.S. Pat. No. 6,528,989. Thus, the unit 24 shall not be described here in greater detail. However, the unit 24 is simplified relatively to the prior art synchronous detectors since it is not necessary to set up components in quadrature-phase Qx, Qy and Qz.

The unit 24 is connected to an indicator 40 capable of reporting the presence of a magnetic disturber from the amplitude of the component I of the magnetic fields measured. The working of this indicator is described in greater detail with reference to FIG. 2.

The association of the triaxial sensor 10, the uniaxial sources, the unit 24 and the indicator 40 forms a detector of a magnetic field disturber.

The unit 24 is also connected to a module 42 for localizing the object 4 in the referential system 6. Typically, the module 42 determines the position and orientation of the object 4 by resolving a system of equations. This system of equations is obtained by modeling the magnetic interactions between the uniaxial sources and the transducers without taking account of the presence of a disturbers. In this system of equations, the position x, y and z and the orientation $\theta_x$, $\theta_y$ and $\theta_z$ of the object 4 are unknowns while the values of the other parameters are obtained from measurements made by the sensor 40. Further information on such systems of equations can be found for example in the patent application EP 1 502 544.

Here, preferably, this system of equations is written in the form of a Kalman filter.

For example, the unit 24 takes the form of an electronic board while the indicator 40 and the module 42 take the form of software modules. To this end, the system 2 includes a programmable electronic computer 44 incorporating the unit 24 and capable of executing instructions recorded on an information-recording medium. The computer 42 is connected to a memory 46 containing the instructions for executing the method of FIG. 2 or 4 when they are executed by the computer 44. The computer 44 is also connected to a man-machine interface 48. For example, the man-machine interface has a screen on which the position of the object 4 in the reference system 6 is presented.

The system 2 may also have other apparatuses for measuring physical quantities, other than magnetic fields, representing the position of the object 4 in the referential system 6. For example, the system 2 includes an apparatus 50 such as a radiography apparatus or a camera. The measurements made by the apparatus 50 are insensitive to the presence or absence of a magnetic disturber.

The working of the system 2 shall now be described in greater detail with reference to the method of FIG. 2.

Before the object 4 is localized in the referential system 6, a phase 60 is performed for detecting disturbers. At the beginning of this phase, during a step 62, the uniaxial source 32 sends out fields $B_{11}, B_{12}, \ldots B_{1j}$ of the same amplitude $A_{1j}$ but respectively at different frequencies $f_1, f_2, \ldots f_j$. Thus, the ratio between the amplitudes of the magnetic fields emitted is constant and equal to one. For example, the frequencies $f_j$ are chosen in a range of values from 10 Hz to 100 kHz. Preferably, they are evenly distributed in the selected range. These fields $B_{1j}$ may be emitted simultaneously or sequentially, i.e. one after the other.

At the same time, at a step 64, the amplitude $Am_{1j}$ of the magnetic fields $B_{1j}$ is measured by means of the sensor 10 and the unit 24.

Then the indicator 40 makes a check to see if the ratios between the amplitudes $A_{1j}$ for different frequencies are substantially equal between the ratios $Am_{1j}$ for these same frequencies. Since here the ratios between the amplitudes $A_{1j}$ are all equal to one, this verification amounts to a check on whether the amplitudes $Am_{1j}$ measured at different frequencies are substantially equal whatever the frequency.

Many methods are possible to make this verification. For example here, the indicator 40, in a step 66, computes a ratio $r_{1j}$ using the following formula:

$$r_{1j} = Am_{1j}/Am_{11}$$

This ratio $r_{1j}$ is computed for all the frequencies $f_j$ of the magnetic fields emitted by the uniaxial source 32.

Figure 3:
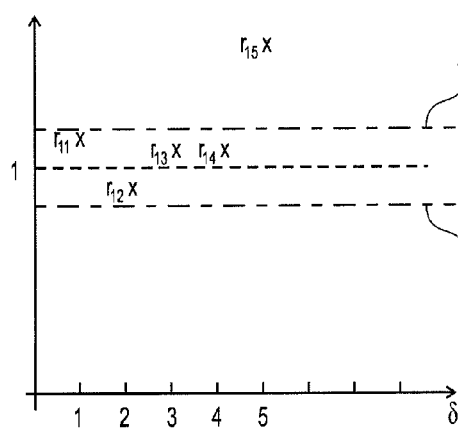
FIG. 3 is a graph illustrating the implementation of the procedure of FIG. 2.

Then, at a step 68, each ratio $r_{1j}$ is compared with a minimum threshold $S_{min}$ and a maximum threshold $S_{max}$. These thresholds $S_{min}$ and $S_{max}$ are situated on either side of the theoretical value of the ratio $r_{1j}$ in the absence of a disturber (see FIG. 3). In this example, the theoretical value is one. Here, the thresholds $S_{min}$ and $S_{max}$ are chosen so as to enable a tolerance of less than 10% around this theoretical value. For example, a tolerance of at least 3% is planned here. For example, the thresholds $S_{min}$ and $S_{max}$ are respectively below 0.95 and above 1.05.

If one of the ratios $r_{1j}$ is not contained between the thresholds $S_{min}$ and $S_{max}$, then a step 70 is performed to report the presence of an amplitude disturber. At the step 70, this piece of information is presented to an individual through the man-machine interface 48. If not, no disturber is reported.

The steps 62 to 70 are reiterated for each measurement pair. These iterations can be done sequentially, i.e. one after another, or in parallel, i.e. at the same time.

Once the detection phase 60 has been done for each measurement pair, a phase 80 is performed for localizing the object 4. At the beginning of this phase, at a step 82, each uniaxial source sends out two magnetic fields $B_{im}$. Preferably, the magnetic fields $B_{im}$ are sent respectively at working frequencies $f_{1t}$ and $f_{2t}$ chosen from among the frequencies $f_j$ used at the step 62.

At the same time, at a step 84, these magnetic fields $B_{im}$ are measured by means of the sensor 10 and the unit 24.

The steps 82 to 84 can be done for a measurement pair one after the other or for all the measurement pairs simultaneously.

Once the measurements have been made, they are given to the module 42 which carries out a step 86 for determining the localization of the object in the referential system 6. At this step 86, the different values measured are used to parametrize the system of equations that must then be resolved. Since we have 18 measurement pairs available and since only nine measurement pairs are needed to resolve this system of equations, there are a great many pieces of redundant information available. This redundancy of information is put to use by the module 42 by the weighting of the disturbed measurements i.e. the measurements obtained by a measurement pair reported as being disturbed at the step 70, by means of a coefficient which restricts the impact of this disturbed measurement on the localizing of the object 4. More specifically, this coefficient diminishes the importance of the measurements disturbed relatively to the other measurements which have not been reported as being disturbed. This weighting coefficient may be non-zero. It may also take the value zero which amounts to quite simply not taking account of the measurements disturbed when determining the localizing of the object 4.

Figure 2:
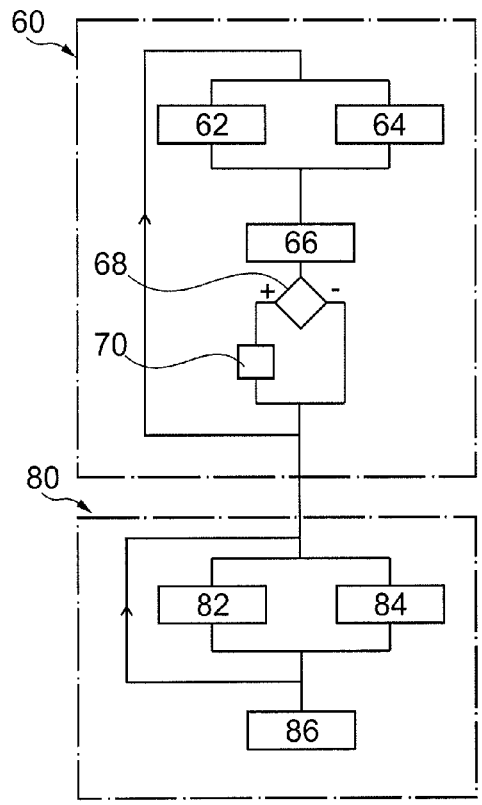
FIG. 2 is a flowchart of a method for localizing by means of the system of FIG. 1.
Figure 4:
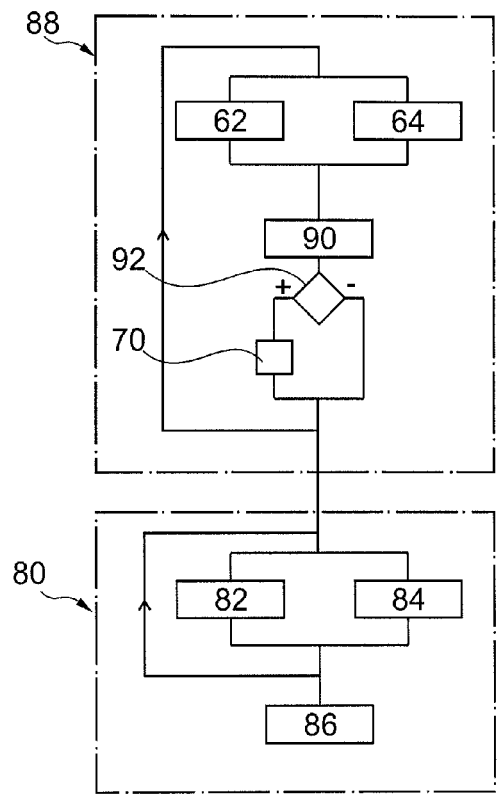
FIG. 4 is a flowchart of another embodiment of a method for localizing by means of the system of FIG. 1.

FIG. 4 represents a variant of the method of FIG. 2. This variant is identical to the variant of FIG. 2 except that the phase 60 for detecting a disturber is replaced by a phase 88.

The phase 88 is distinguished from the phase 60 in that the detection of the fact that the amplitudes $A_{1j}$ are appreciably constant whatever the frequency $f_j$ is done differently. To this end, the steps 66 and 68 are replaced respectively by the steps 90 and 92.

Figure 5:
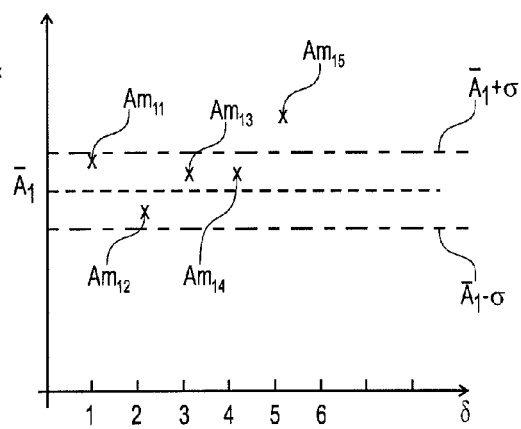
FIG. 5 is a graph illustrating the implementation of the method of FIG. 4.

At the step 90, the mean $\overline{A}_1$ of the amplitudes $Am_{1j}$ measured is computed. During this step, the standard deviation $\sigma$ relatively to this mean is also computed. The amplitude $Am_{1j}$ is the amplitude of the component I in phase of the magnetic field. Then, at a step 92, it is ascertained that each amplitude $Am_{1j}$ is included between the thresholds defined as a function of $\overline{A}_1$ and the standard deviation $\sigma$. For example, these thresholds are $\overline{A}_1 - \sigma$ and $\overline{A}_1 + \sigma$. If one of the amplitudes $Am_{ii}$ measured is not included between the thresholds $\overline{A}_1 - \sigma$, $\overline{A}_1 + \sigma$, then the method proceeds to the step 70. If not, no disturber is reported. This way of checking that the amplitudes $Am_t$ are appreciably constant whatever the frequency $f_j$ is shown in FIG. 5. In FIG. 5, the crosses represent the amplitudes $Am_{1j}$ measured.

This graph especially shows the reporting of a disturber since the amplitude $Am_{15}$ is above the amplitude $\overline{A}_1 + \sigma$.

The steps 90 and 92 are another way of checking that the ratios between the amplitudes measured for different frequencies are appreciably constant whatever the frequency in the absence of the disturber.

Numerous other embodiments are possible. For example, it is possible to use the amplitude Ch of the modulus of the field instead of the amplitude of the component I, regardless of whether the disturber is a conductive part or a magnetic part. In this case, the components I and Q must be measured. However, only the amplitude of the component I can be used if the disturber is a non-conductive magnetic part.

The localizing and detection of the disturbers has been described here in the particular case where it is the object 4 that is mobile relatively to a fixed referential system 6. What has been described earlier also applies to the inverse situation where it is the object 4 that is fixed and the referential system 6 that is mobile. In this case, the object 4 is fixed and it is the uniaxial sources that are shifted relatively to the object 4.

It is also possible to invert the position of the sources and of the sensors. For example, one or more triaxial magnetic field sources can be integrated into the object and one or more triaxial sensors can be fixed without any degree of freedom to the referential system 6.

What has been described earlier also applies to systems for localizing the object 4 in a referential system with one or two dimensions. Similarly, the system 2 can be simplified if it is not sought to measure the position or orientation of the object 4. In these cases, the number of measurement pairs may be reduced.

The magnetic fields $B_{ij}$ can be time multiplexed or frequency multiplexed. Thus it is possible, in the case of frequency multiplexing, to conduct in parallel several iterations of the steps 62 to 70 for different fields of different frequencies.

It is not necessary for the magnetic fields emitted by a coil to be all of the same amplitude whatever the frequency. Indeed, if the amplitude of the magnetic field $B_{ij}$ varies as a function of its frequency, it is then necessary to know the ratio between the amplitudes of the magnetic fields emitted by this coil at different frequencies to verify the fact that the ratios of the amplitudes measured remain close to the expected ratios. For example, the expected ratio between the measured amplitudes of the magnetic fields for different frequencies is determined from the intensity of the current supplying the coils forming the uniaxial sources 32 to 34. These expected ratios may also be determined during a phase of calibration in the absence of a disturber.

The frequencies $f_j$ used during the phase 60 for detecting a disturber are, as a variant, chosen in frequency bands free of electromagnetic parasites. For example, the device identifies bands free of electromagnetic parasites by listening to the magnetic fields already present in the environment before starting the detection of a disturber.

When a disturber is detected, it is possible to replace the disturbed measurements from the measurements obtained from the apparatus 50 or to take account additionally of the measurements obtained from the apparatus 50.

The orientation of the object to be localized can be defined by another method such as methods using Euler angles and quaternions.

What has been described above cannot be applied solely to the medical field but on the contrary to any field where it is necessary to detect a disturber or to locate an object by using magnetic fields.

The invention claimed is:

1. A method for detecting a disturber of an amplitude of a magnetic field amplitude, the disturber being in proximity to a uniaxial magnetic field source, said method comprising:
    emitting several magnetic fields from the uniaxial magnetic field source, said several magnetic fields being emitted at at least three different frequencies, $f_1, f_2, \ldots f_j$, wherein, of said several magnetic fields emitted, two magnetic fields having different unspecified frequencies chosen among said at least three different frequencies $f_1, f_2, \ldots f_j$, have amplitudes when emitted being related to each other by a predetermined ratio, which ratio is constant and equal to one,
    using a sensor spaced from said uniaxial magnetic field source, measuring amplitudes of said two magnetic fields emitted at said different unspecified frequencies, and reporting an amplitude disturber when a ratio between the measured amplitudes of said two magnetic fields emitted diverges from one by a predetermined threshold.

2. The method of claim 1, wherein the ratios between the amplitudes of the magnetic fields emitted at the different frequencies are all equal.

3. The method of claim 1, further comprising:
    synchronizing the emission and the measurements of the magnetic fields of different frequencies to measure only the amplitude of the magnetic fields in phase with the magnetic fields emitted at said different frequencies, and
    determining whether to report or not report an amplitude disturber solely as a function of the measured amplitudes of the magnetic fields in phase.

4. The method of claim 1, wherein emitting several magnetic fields at different frequencies comprises emitting magnetic fields of different frequencies simultaneously.

5. A method for localizing an object in a referential system using at least one measurement pair, each measurement pair including a uniaxial source capable of emitting magnetic fields at several frequencies, and a sensor to measure the amplitude of the magnetic fields emitted by the uniaxial source, one among the uniaxial source and the sensor being linked to the referential system while the other among the uniaxial source and the sensor being linked to the object, said method comprising:
    emitting, using the uniaxial source of a measurement pair, a magnetic field at a given frequency, and
    measuring, using the sensor of the measurement pair, the magnetic field,
    localizing the object in the referential system from measurements made by at least the measurement pair,
    detecting a disturber of amplitude of the magnetic field by using the uniaxial source and the sensor of the measurement pair to implement the method of claim 1, and
    when the object is localized, weighting the measurement of the magnetic field made by the measurement pair as a function of whether or not a disturber is reported so as to limit impact of a disturbed measurement made by the measurement pair on the localizing of the object.

6. The method of claim 5, wherein emitting and measuring comprise:
    emitting magnetic fields and measuring magnetic fields using more than nine measurement pairs, each measurement pair being distinguished from other measurement pairs by one of the uniaxial source, the sensor used, and the frequency of the measured magnetic field measured, and
    when the object is localized, weighting the measurement by a measurement pair reported as being disturbed by a disturber so as to limit the impact of the disturbed measurement on the localizing of the object relative to the non-disturbed measurements of the measurement pair.

7. A manufacture comprising a tangible and non-transitory computer-readable medium having encoded thereon software for detecting a disturber of an amplitude of a magnetic field amplitude in proximity to a uniaxial magnetic field source, said software including instructions that, when executed by a computer, cause:
    emitting of several magnetic fields from the uniaxial magnetic field source, said several magnetic fields being emitted at at least three different frequencies, $f_1, f_2, \ldots f_j$, wherein, of said the several magnetic fields emitted, two magnetic fields having different unspecified frequencies chosen among said at least three different frequencies $f_1$, $f_2, \ldots f_j$, have amplitudes when emitted being related to each other by a predetermined ratio, which ratio is constant and equal to one, using a sensor, spaced from said uniaxial magnetic field source, measuring amplitudes of said two magnetic fields emitted at said different unspecified frequencies, and reporting of an amplitude disturber when a ratio between said two measured amplitudes diverges from one by a predetermined threshold.

8. An apparatus for detecting a disturber of magnetic field amplitude, comprising:

- a uniaxial magnetic field source configured to emit several magnetic fields at at least three different frequencies, $f_1$, $f_2$, $f_j$, wherein, of said several magnetic fields emitted, two magnetic fields having different unspecified frequencies chosen among said at least three different frequencies, $f_1$, $f_2$, $f_j$, have amplitudes when emitted being related to one another by a predetermined ratio, which ratio is constant and equal to one,
- a sensor, spaced from said uniaxial magnetic field source, to measure amplitudes of said two magnetic fields emitted at said different unspecified frequencies, and
- an indicator configured to report presence of a disturber of amplitude of the magnetic field only if a ratio between the measured amplitudes of said two magnetic fields emitted diverges from one by a predetermined threshold.

9. The apparatus of claim 8, wherein the uniaxial source comprises a single coil having turns wound about a single winding axis.

10. The apparatus of claim 8, further comprising a system for localizing an object in a referential system, said system including:
- at least one measurement pair, each measurement pair having a uniaxial source capable of emitting magnetic fields at several frequencies, and a sensor capable of measuring amplitudes of magnetic fields emitted by the uniaxial source, one among the uniaxial source and the sensor being linked to the referential system and the other among the uniaxial source and the sensor being linked to the object; and
- a localization module capable of localizing the object in the referential system from measurements made by the measurement pair or pairs, and weighting the measurement of the magnetic field made by the measurement pair as a function of the reporting or non-reporting of a disturber so as to limit the impact of a disturbed measurement made by the measurement pair on the localizing of the object;
- wherein the uniaxial source and the sensor of the detector is common with those of the measurement pair.

* * * * *